US011472738B2

(12) United States Patent
Hill et al.

(10) Patent No.: US 11,472,738 B2
(45) Date of Patent: Oct. 18, 2022

(54) METHODS FOR THE MANUFACTURE OF COLORFAST MASONRY

(71) Applicant: BIOMASON, INC., Research Triangle Park, NC (US)

(72) Inventors: Thomas A. Hill, Dacula, GA (US); Steven W. McAllister, Durham, NC (US); J. Michael Dosier, Raleigh, NC (US); Ginger K. Dosier, Raleigh, NC (US)

(73) Assignee: BIOMASON INC., Durham, NC (US)

( * ) Notice: Subject to any disclaimer, the term of this patent is extended or adjusted under 35 U.S.C. 154(b) by 0 days.

(21) Appl. No.: 16/923,558

(22) Filed: Jul. 8, 2020

(65) Prior Publication Data

US 2020/0331804 A1 Oct. 22, 2020

Related U.S. Application Data

(60) Division of application No. 15/455,689, filed on Mar. 10, 2017, now Pat. No. 10,717,674, which is a continuation-in-part of application No. 15/066,692, filed on Mar. 10, 2016, now abandoned.

(60) Provisional application No. 62/188,556, filed on Jul. 3, 2015, provisional application No. 62/130,854, filed on Mar. 10, 2015, provisional application No. 62/200,288, filed on Aug. 3, 2015.

(51) Int. Cl.
| | |
|---|---|
| *C04B 20/10* | (2006.01) |
| *C12P 3/00* | (2006.01) |
| *C12N 11/14* | (2006.01) |
| *B05D 1/02* | (2006.01) |
| *C12N 11/02* | (2006.01) |
| *C04B 28/10* | (2006.01) |
| *C04B 12/00* | (2006.01) |
| *C04B 111/60* | (2006.01) |
| *C04B 103/00* | (2006.01) |
| *C04B 111/00* | (2006.01) |

(52) U.S. Cl.
CPC .......... *C04B 20/1092* (2013.01); *B05D 1/02* (2013.01); *C04B 12/00* (2013.01); *C04B 28/10* (2013.01); *C12N 11/02* (2013.01); *C12N 11/14* (2013.01); *C12P 3/00* (2013.01); *C12Y 305/01005* (2013.01); *C04B 2103/0001* (2013.01); *C04B 2103/0075* (2013.01); *C04B 2111/00146* (2013.01); *C04B 2111/60* (2013.01); *Y02W 30/91* (2015.05)

(58) Field of Classification Search
CPC .......... C12N 11/14; C12N 1/20; C12N 11/02; C04B 2111/00146; C04B 28/10; C04B 2103/0001; C04B 2103/0075; C04B 12/00; C04B 20/1092; C04B 2111/60; C04B 14/04; C04B 14/22; C04B 14/34; C04B 18/20; C04B 18/241; C04B 18/26; C04B 38/10; C04B 14/06; C04B 18/12; C04B 18/16; C04B 18/24; C12P 3/00; C12Y 305/01005; Y02W 30/91; B05D 1/02

See application file for complete search history.

(56) References Cited

U.S. PATENT DOCUMENTS

| | | | |
|---|---|---|---|
| 3,667,976 | A | 6/1972 | Tanner et al. |
| 3,829,553 | A | 8/1974 | Lynn |
| 4,204,876 | A | 5/1980 | Bowden |
| 4,617,326 | A | 10/1986 | Bjornberg et al. |
| 4,946,505 | A | 8/1990 | Jungk |
| 5,143,155 | A | 9/1992 | Ferris et al. |
| 5,199,986 | A | 4/1993 | Krockert et al. |
| 5,558,708 | A | 9/1996 | Johansen, Jr. et al. |
| 5,846,315 | A | 12/1998 | Johansen, Jr. et al. |
| 5,891,205 | A | 4/1999 | Picardi et al. |
| 6,348,147 | B1 | 2/2002 | Long |

(Continued)

FOREIGN PATENT DOCUMENTS

| | | |
|---|---|---|
| CA | 2591097 A1 | 6/2006 |
| CN | 1101626 A | 4/1995 |

(Continued)

OTHER PUBLICATIONS

Metayer-Levrel et al., Applications of bacterial carbonatogenesis to the protection and regeneration of limestones in buildings and historic patrimony. Sedimentary Geology., 1999, vol. 126: 25-34. (Year: 1999).*

(Continued)

*Primary Examiner* — Ganapathirama Raghu
(74) *Attorney, Agent, or Firm* — Wilson Sonsini Goodrich & Rosati

(57) ABSTRACT

The invention is directed to compositions and methods for the manufacture of pigmented solids structures for which can be used for construction and/or decoration. Manufacturing comprises fixing one or more pigments to an aggregate material such as crushed rock, stone or sand. The pigmented aggregate is incubated with urease or urease producing microorganisms, an amount of a nitrogen source such as urea, and an amount of calcium source such as calcium chloride forming calcite bridges between particles of aggregate. The resulting solid has a hardness and colorfastness for most any construction material. Using selected aggregate and pigment, the process also provides for the manufacture of simulated-stone materials such as clay or granite bricks or blocks, marble counter-tops, and more. The invention is also directed to composition containing microorganisms and pigment as kits that can be added to most any aggregate materials.

18 Claims, No Drawings

(56) References Cited

U.S. PATENT DOCUMENTS

| | | |
|---|---|---|
| 7,025,824 B2 | 4/2006 | Axen et al. |
| 7,101,430 B1 | 9/2006 | Pike et al. |
| 8,182,604 B2 | 5/2012 | Kucharski et al. |
| 8,420,362 B2 | 4/2013 | Crawford et al. |
| 8,470,275 B2 | 6/2013 | Constantz et al. |
| 8,518,177 B2 | 8/2013 | Chattopadhyay et al. |
| 8,728,365 B2 | 5/2014 | Dosier |
| 8,911,549 B2 | 12/2014 | Jonkers |
| 8,912,244 B2 | 12/2014 | Vitomir et al. |
| 8,932,400 B2 | 1/2015 | Chen et al. |
| 8,951,786 B1 | 2/2015 | Dosier |
| 9,074,134 B2 | 7/2015 | Bang et al. |
| 9,199,880 B2 | 12/2015 | Dosier |
| 9,428,418 B2 | 8/2016 | Dosier |
| 9,796,626 B2 | 10/2017 | Dosier |
| 10,125,303 B2 | 11/2018 | Wilson et al. |
| 10,450,695 B2 | 10/2019 | Dosier et al. |
| 10,626,547 B2 | 4/2020 | Dosier et al. |
| 10,717,674 B2 | 7/2020 | Hill et al. |
| 11,008,591 B2 | 5/2021 | Dosier et al. |
| 2005/0029187 A1 | 2/2005 | Koga et al. |
| 2005/0103204 A1 | 5/2005 | Halliday et al. |
| 2005/0103234 A1 | 5/2005 | McNulty, Jr. |
| 2007/0216058 A1 | 9/2007 | Carreras-Maldonado et al. |
| 2008/0245272 A1 | 10/2008 | Kucharski et al. |
| 2010/0086367 A1 | 4/2010 | Darson-Baulleur et al. |
| 2010/0210745 A1 | 8/2010 | McDaniel et al. |
| 2011/0011303 A1 | 1/2011 | Jonkers |
| 2011/0027850 A1 | 2/2011 | Crawford et al. |
| 2011/0262640 A1 | 10/2011 | Dosier |
| 2012/0199046 A1 | 8/2012 | Jonkers |
| 2013/0112114 A1 | 5/2013 | Jonkers |
| 2013/0196419 A1 | 8/2013 | Chavez Crooker et al. |
| 2014/0239535 A1 | 8/2014 | Dosier |
| 2014/0248681 A1* | 9/2014 | Soens .................. C12N 11/04 435/182 |
| 2014/0369749 A1* | 12/2014 | Friedman ............... C09K 17/40 404/72 |
| 2015/0264898 A1 | 9/2015 | Ortego et al. |
| 2015/0322604 A1 | 11/2015 | Brunner et al. |
| 2016/0010434 A1 | 1/2016 | Portman et al. |
| 2016/0068438 A1 | 3/2016 | Dosier |
| 2016/0090328 A1 | 3/2016 | Wiktor et al. |
| 2016/0130489 A1 | 5/2016 | Gilmour |
| 2016/0174530 A1 | 6/2016 | Barber |
| 2016/0264463 A1 | 9/2016 | Dosier et al. |
| 2016/0362334 A1 | 12/2016 | Dosier |
| 2017/0015832 A1 | 1/2017 | Berlin et al. |
| 2017/0190617 A1 | 7/2017 | Hill et al. |
| 2017/0190620 A1 | 7/2017 | Jonkers et al. |
| 2018/0118623 A1 | 5/2018 | Smith et al. |
| 2018/0244585 A1 | 8/2018 | Rahbar et al. |
| 2018/0305858 A1 | 10/2018 | Dosier et al. |
| 2019/0106716 A1 | 4/2019 | Dosier et al. |
| 2019/0106717 A1 | 4/2019 | Dosier et al. |
| 2019/0210924 A1 | 7/2019 | Royne et al. |
| 2020/0171533 A1 | 6/2020 | Dosier et al. |
| 2020/0262711 A1 | 8/2020 | Dosier et al. |
| 2020/0346976 A1 | 11/2020 | Hill et al. |
| 2021/0189238 A1 | 6/2021 | Kavazanjian et al. |

FOREIGN PATENT DOCUMENTS

| | | |
|---|---|---|
| CN | 1125472 A | 6/1996 |
| CN | 1285401 A | 2/2001 |
| CN | 1778934 A | 5/2006 |
| CN | 1807358 A | 7/2006 |
| CN | 101270369 A | 9/2008 |
| CN | 101054568 B | 5/2010 |
| CN | 102121033 A | 7/2011 |
| CN | 102587875 A | 7/2012 |
| CN | 103173376 A | 6/2013 |
| CN | 103173376 B | 10/2014 |
| CN | 104071890 A | 10/2014 |
| CN | 105080932 A | 11/2015 |
| CN | 105418013 A | 3/2016 |
| CN | 105837075 A | 8/2016 |
| CN | 105884308 A | 8/2016 |
| CN | 105924053 A | 9/2016 |
| CN | 105925512 A | 9/2016 |
| CN | 108956667 A | 12/2018 |
| EP | 0388304 A1 | 9/1990 |
| EP | 0631998 A1 | 1/1995 |
| EP | 1838642 A1 | 10/2007 |
| EP | 1893546 A1 | 3/2008 |
| EP | 2082999 A1 | 7/2009 |
| EP | 2247551 A1 | 11/2010 |
| EP | 2297062 A1 | 3/2011 |
| EP | 2429970 A1 | 3/2012 |
| EP | 2462232 A2 | 6/2012 |
| EP | 2940122 A1 | 11/2015 |
| JP | S63227330 A | 9/1988 |
| JP | H05253908 A | 10/1993 |
| JP | 2006144285 A | 6/2006 |
| JP | 2007284974 A | 11/2007 |
| JP | 2008524096 A | 7/2008 |
| JP | 2009270302 A | 11/2009 |
| JP | 2011509915 A | 3/2011 |
| JP | 2012019751 A | 2/2012 |
| JP | 2013523590 A | 6/2013 |
| JP | 5253908 B2 | 7/2013 |
| JP | 5284646 B2 | 9/2013 |
| JP | 2014510689 A | 5/2014 |
| WO | WO-0248069 A1 | 6/2002 |
| WO | WO-03055450 A1 | 7/2003 |
| WO | WO-2006066326 A1 | 6/2006 |
| WO | WO-2007044439 A2 | 4/2007 |
| WO | WO-2007070706 A2 | 6/2007 |
| WO | WO-2008009771 A1 | 1/2008 |
| WO | WO-2008120979 A1 | 10/2008 |
| WO | WO-2009009838 A1 | 1/2009 |
| WO | WO-2009093898 A1 | 7/2009 |
| WO | WO-2010130712 A1 | 11/2010 |
| WO | WO-2011126361 A1 | 10/2011 |
| WO | WO-2011137106 A1 | 11/2011 |
| WO | WO-2012113765 A1 | 8/2012 |
| WO | WO-2013120847 A1 | 8/2013 |
| WO | WO-2014185781 A1 | 11/2014 |
| WO | WO-2015042031 A1 | 3/2015 |
| WO | WO-2015155769 A1 | 10/2015 |
| WO | WO-2016010434 A1 | 1/2016 |
| WO | WO-2016144786 A1 | 9/2016 |
| WO | WO-2016145190 A1 | 9/2016 |
| WO | WO-2017139750 A1 | 8/2017 |
| WO | WO-2017189106 A1 | 11/2017 |
| WO | WO-2017220768 A1 | 12/2017 |
| WO | WO-2018064320 A1 | 4/2018 |
| WO | WO-2018081542 A1 | 5/2018 |
| WO | WO-2018200684 A1 | 11/2018 |
| WO | WO-2019071172 A1 | 4/2019 |
| WO | WO-2019071175 A1 | 4/2019 |
| WO | WO-2020168342 A1 | 8/2020 |
| WO | WO-2020180914 A1 | 9/2020 |
| WO | WO-2020198295 A1 | 10/2020 |
| WO | WO-2022010915 A1 | 1/2022 |

OTHER PUBLICATIONS

Phillips et al., Engineered applications of ureolytic biomineralization: a review. Biofouling, 2013, vol. 29(6): 715-733. (Year: 2013).*

Wiktor et al., Quantification of crack-healing in novel bacteria-based self-healing concrete. Cement & Concrete Composites, 2011, vol. 33: 763-770. (Year: 2011).*

Beck et al., On the use of eggshell lime and tuffeau powder to formulate an appropriate mortar for restoration purposes. Geological Society, Jan. 2010, London, Special Publications, 331, 137-145. (Year: 2010).*

Cree et al., Sustainable Bio-Inspired Limestone Eggshell Powder for Potential Industrialized Applications. ACS Sustainable Chem. Eng. 2015, vol. 3: 941-949. (Year: 2015).*

(56) References Cited

OTHER PUBLICATIONS

Hammes et al. Key roles of pH and calcium metabolism in microbial carbonate precipitation. Re/Views in Environmental Science & Bio/Technology 1:3-7 (2002).
Sun et al. Study of magnesium precipitation based on biocementation. Marine Georesources & Geotechnology, 2019, vol. 37, No. 10, pp. 1257-1266. Published online Jan. 29, 2019.
Achal, Varenyam, et al., "Biogenic Treatment Improves the Durability and Remediates the Cracks of Concrete Structures", Construction and Building Materials, 2013, vol. 48, pp. 1-5.
Application of Bacteria as Self-Healing Agent for the Development of Sustainable Concrete, H.M. Jonkers et al., Ecological Engineering 36:230-235, 2010.
Bang et al., "Calcite precipitation induced by polyurethane immobilized Bacillus pasteurii", Enzyme and Microbial Technology, 2001, vol. 28, pp. 404-409.
BioZEment (completed). Web Page. UiO Department of Physics. Published Nov. 3, 2014. Last modified Nov. 27, 2017. Retrieved Oct. 22, 2021 at URL: https://www.mn.uio.no/fysikk/english/research/projects/biozement/. 5 pages.
Bundur et al., Biomineralized cement-based materials: impact of inoculating vegetative bacterial cells on hydration and strength. Cement and Concrete Res., 2015, vol. 67: 237-245. Available online Oct. 27, 2014.
Castro-Alonso et al., Microbially Induced Calcium Carbonate Precipitation (MICP) and Its Potential in Bioconcrete: Microbiological and Molecular concepts. Frontiers in Materials, 2019, vol. 6, Article 126: 1-15.
Chekroun et al. Precipitation and Growth Morphology of Calcium Carbonate Induced by Myxococcus Xanthus: Implications for Recognition of Bacterial Carbonates. Journal of Sedimentary Research 74 (6): 868-876 (2004).
Cho et al, "Effect of Surfactants on CO2 Biomineralization with *Sporosarcina pasteurii* and *Bacillus megaterium*", Water Air Soil Pollut., 2015, vol. 226:2245, pp. 1-12.
Choi, Sun-Gyu, et al., "Biocementation for Sand Using an Eggshell as Calcium Source", Journal of Geotech, Journal of Geotechnical and Geoenvironmental Engineering, Technical Note, 2016, pp. 1-4.
Choi, Sun-Gyu, et al., "Properties of Biocemented, Fiber Reinforced Sand", Construction and Building Materials, 2016, vol. 120, pp. 623-629.
Chu, Jian, et al., "Proof of Concept: Biocement for Road Repair", Final Report, Mar. 2015, Iowa State University, Midwest Transportation Center, 15 Pages.
Chu, Jian, "Solutions to Sustainability in Construction: Some Examples", Procedia Engineering, 2016, vol. 145, pp. 1127-1134.
Cichoż-Lach et al. Current pathogenetic aspects of hepatic encephalopathy and noncirrhotic hyperammonemic encephalopathy. World J Gastroenterol. Jan. 7, 2013;19(1):26-34.
Co-pending U.S. Appl. No. 16/933,171, inventors Hill; Thomas A. et al., filed Jul. 20, 2020.
Co-pending U.S. Appl. No. 17/322,179, inventors Dosier; Ginger K. et al., filed May 17, 2021.
Cunningham, A.B., et al., "Reducing the Risk of Well Bore Leakage of CO2 Using Engineered Biomineralization Barriers", Energy Procedia, 2011, vol. 4, pp. 5178-5185.
Cuzman et al., Bacterial "Masons" at work with wastes for producing eco-cement. Int. J. Environ. Sci. Develop., 2015, vol. 6(10): 767-774.
Day, Jeremy L. et al, Microbiologically Induced Sealant for Concrete Crack Remediation, https://www.ce.washingtonedu/em2003/proceedings/papers/352.pdf (2003).
De Muynck, Willem et al, Microbial Carbonate Precipitation in Construction Materials: A Review, Ecological Engineering, 2010, pp. 118-136, vol. 36, Elsevier.
Dejong, Jason T. et al, Bio-mediated Soil Improvement; Ecological Engineering, 2009, pp. 197-210, vol. 36, Elsevier.
Dejong, Jason T. et al, Microbially Induced Cementation to Control Sand Response to Undrained Shear, Journal of Geotechnical and Geoenvironmental Engineering, Nov. 2006, pp. 1381-1392, ASCE.

F. D. Meyer et al, "Microbiologically-Induced Soil Stabilization: Application of *Sporosarcina pasteurii* for Fugitive Dust Control", GEO-FRONTIERS 2011, Reston, VA, (Mar. 11, 2011), doi:10.1061/41165(397)409, ISBN 978-0-7844-1165-0, pp. 4002-4011, XP055562331.
Ferris, F.G et al, Bacteriogenic Mineral Plugging, Petroleum Society of CIM and CANMET, Paper No. 11, presented at the CIM/CANMET Fourth Petroleum Conference held in Regina, Sask., pp. 11-1 to 11-12, Oct. 7-9, 1991.
Fritzges, Michael B. et al, Biologically Induced Improvement of Loose Sand, Proceedings of the 8th U.S. National Conference on Earthquake Engineering, Apr. 18-22, 2006, Paper No. 1691, San Francisco, US.
Fujita, Yoshiko, et al., Evaluating the Potential of Native Ureolytic Microbes to Remediate a 90Sr Contaminated Environment, Environmental Science & Technology, 2010, vol. 44, No. 19, pp. 7652-7658.
Fukue et al, Grain growth of carbonates using ureolytic microbes, Japanese Geotechnical Journal, (2011), vol. 6, No. 3, pp. 455-464, with English translation of abstract.
Ghosh, P., et al, "Use of Microorganism to Improve the Strength of Cement Mortar", Cement and Concrete Research, 2005, vol. 35, pp. 1980-1983.
Gleb B. Sukhorukov et al., "Porous calciumcarbonate microparticles as templates for encapsulation of bioactive compounds" J. Mater. Chem. 14:2073-2081, 2004.
Gollapudi, U.K. et al, A New Method for Controlling Leaching Through Permeable Channels, Chemosphere, 1995, pp. 695-705, vol. 30, No. 4, Elsevier Science Ltd., Great Britain.
Ivanov et al., "Calcite/aragonite-biocoated artificial coral reefs for marine parks", AIMS Environmental Science, Aug. 22, 2017, vol. 4 (4), pp. 586-595.
Ivanov et al., Chapter 7, Biocementation and Biocements. Construction Biotechnol., Green Energy and Technol., Chapter 7, 2017, pp. 109-138.
Jonkers, Henk M., et al., "A Two Component Bacteria-Based Self-Healing Concrete", Proceedings of the 2nd International Conference on Concrete Repair, Rehabilitation and Retrofitting (ICCRRR), Cape Town, South Africa, Nov. 24-26, 2008. Concrete Repair, Rehabilitation and Retrofitting II, pp. 119-120, Taylor & Francis Group, London.
Kalantary et al., Evaluation of the ability to control biological precipitation to improve sandy soils. Procedia Earth. Planet. Sci., 2015, vol. 15:278-284.
Kantzas, A. et al, A Novel Method of Sand Consolidation Through Bacteriogenic Mineral Plugging, Petroleum Society of CIM, Jun. 7-10, 1992, pp. 46-1-46-15, Paper No. CIM 92-46.
Kim et al. Calcium Carbonate Precipitation by Bacillus and Sporosarcina Strains Isolated from Concrete and Analysis of the Bacterial Community of Concrete. J. Microbiol. Biotechnol. (2016), 26(3), 540-548. First published online Dec. 23, 2015.
Kim et al. Microbially mediated calcium carbonate precipitation on normal and lightweight concrete. Construction and Building Materials, vol. 38, pp. 1073-1082 (2013). Available online Nov. 6, 2012.
Kurizaki et al, "A Case of Stone Formation in the Mainz Pouch using Appendix as the Efferent Limb: A Case Report", Nihon Hinyokika Gakkai Zasshi. The Japanese Journal of Urology, 2002, vol. 93(4), pp. 573-576. (English translation of abstract.).
Ibtisam A. Hammad et al., Urease activity and induction of calcium carbonate precipitation by Sporosarcina pasteurii NCIMB 8841; Journal of Applied Sciences Research 9(3): 1525-33, 2013.
Le Metayer-Levrel G, et al, "Applications of bacterial carbontogenesis to the protection and regeneration of limestones in building and historic patrimony," Sedimentary Geology, Jul. 31, vol. 126, No. 1, pp. 26, 29, 32-33 (1999).
MAZRIA. It's the Architecture, Stupid! pp. 48-51. Retrieved Aug. 29, 2021 from URL: https://backspace.com/notes/images/its_the_architecture.pdf. May/Jun. 2003.
Meyer et al., "Microbiologically-Induced Soil Stabilization: Application of Sporosarcina pasteurii for Fugitive Dust Control", Geo-Frontiers Congress 2011, pp. 4002-4011.

(56) References Cited

OTHER PUBLICATIONS

Nemati, M. et al, Modification of Porous Media Permeability, Using Calcium Carbonate Produced Enzymatically In Situ, Enzyme and Microbial Technology, 2003, pp. 635-642, vol. 33, Elsevier.
Park et al., "Effect of Plant-Induced Calcite Precipitation on the Strength of Sand", Journal of Materials in Civil Engineering, 2014, vol. 26, Issue 8.
PCT Search and Patentability Report for PCT/US2016/21763, dated Jun. 2, 2016.
PCT Search and Patentability Report for PCT/US2017/21833, dated Jun. 9, 2017.
PCT/EP2017/065509 International Preliminary Report on Patentability dated Dec. 25, 2018.
PCT/US2017/021833 International Preliminary Report on Patentability dated Sep. 11, 2018.
PCT/US2017/021833 Written Opinion dated Jun. 9, 2017.
Phillips A.J., Biofilm-induced calcium carbonate precipitation: Application in the subsurface. Ph. D., Dissertation, Montana State University, Nov. 2013, pp. 1-241.
Phua, Y.J., et al., "Morphology and Polymorphism of Calcium Carbonate Precipitated from Different Calcium Sources Via Enzyme Induced Carbonate Precipitation", Department of Physics, University of Oslo, Norway, 2016, Goldschmidt Conference Abstracts—1 Page.
Pinar et al, "Bacterial Community Dynamics During the Application of a *Myxococcus xanthus*-Inoculated Culture Medium Used for Consolidation of Ornamental Limestone", Microb.Ecol., 2010, vol. 60, pp. 15-28.
Reddy et al. Embodied energy of common and alternative building materials and technologies. Energy and Buildings, vol. 35, Issue 2, pp. 129-137 (2003).
Remediation of Concrete Using Microorganisms, S.K. Ramachandran et al., ACI Materials Journal Jan./Feb. 2001.
Rodriguez-Navarro, Carlos, et al., "Influence of Substrate Mineralogy on Bacterial Mineralization of Calcium Carbonate: Implications for Stone Conservation", Applied and Environmental Microbiology, Jun. 2012, vol. 78, No. 11, pp. 4017-4029.
Romillac N., Ammonification. Encyclopedia of Ecology, 2nd edition, 2019, vol. 2: 256-263.
Stabnikov et al., "Immobilization of Sand Dust and Associated Pollutants Using Bioaggregation", Water, Air, & Soil Pollution, 2013, vol. 224, 1631.
Stabnikov, Viktor, et al., "Halotolerant, Alkaliphilic Urease-Producing Bacteria from Different Climate Zones and their Application for Biocementation of Sand", World Journal of Microbiology and Biotechnology, 2013, vol. 29, pp. 1453-1460.
Stocks-Fischer, Shannon et al, Microbiological Precipitation of CaCO3, Soil Biology and Biochemistry, 1999, pp. 1563-1571, vol. 31, Elsevier Science Ltd.
Streamer, M., "Urea and Arginine metabolism in the Hard Coral, Acropora acuminata", Comp. Biochem. Physiol., vol. 65B, pp. 669 to 674, 1980.
Talaiekhozani et al., "Application of Proteus mirabilis and Proteus vulgaris mixture to design self-healing concrete", Desalination and Water Treatment, 2014, vol. 52, pp. 3623-3630.
The Better Brick, 2010 Next Generation Winner (https://www.metropolismag.com/uncategorized/the-better-brick-2010-next-generation-winner/).
Therkildsen et al., Urea production by the marine bacteria *Delaya venusta* and *Pseudomonas stutzeri* grown in minimal medium, Aquatic Microbial Ecology, vol. 13:213-217 (1997).
Through the Sandglass, (http://throughthesandglass.typepad.com/through_the_sandglass/2010/07/sandbacteriaurinebricks-continuing-performances-of-bacillus-pasteurii.html) Jul. 19, 2010.

T.K. Ghose et al., "Studies on fibre-entrapped whole microbial cells in urea hydrolysis," Enzyme and Microbial Technology, vol. 1, No. 1, pp. 47-50, Jan. 1, 1979.
U.S. Appl. No. 15/455,689 Notice of Allowance dated Jun. 8, 2020.
U.S. Appl. No. 15/455,689 Office Action dated Jul. 18, 2019.
U.S. Appl. No. 15/455,689 Office Action dated Nov. 25, 2019.
U.S. Appl. No. 15/455,689 Office Action dated Mar. 26, 2020.
Van Paassen, Leon A., et al., "Potential Soil Reinforcement by Biological Denitrification", Ecological Engineering, 2010, vol. 36, pp. 168-175.
Wang et al., Application of microorganisms in concrete: a promising sustainable strategy to improve concrete durability. Appl. Microbial Biotechnol., 2016, vol. 100: 2993-3007.
Whiffin. Victoria S. et al, Microbial Carbonate Precipitation as a Soil Improvement Technique, Geomicrobiology Journal, 2007, pp. 417-423, vol. 24, Taylor & Francis Group, LLC.
Whiffin, Victoria S., Microbial CaCO3 Precipitation for the Production of Biocement, PhD Thesis, 2004, Murdoch University, Western Australia.
Wikipedia, "Shale," Aug. 22, 2018; retrieved on Sep. 13, 2021 from https://en.wikipedia.org/w/index.php?title=Shale&oldid=855968675.
Wikipedia, "Pseudomonas fluorescens," May 15, 2018; retrieved on Sep. 13, 2021 from https://en.wikipedia.org/w/index.php?title-Pseudomonas_fluorescens&oldid=841444300.
Yoosathaporn et al., The influence of biocalcification on soil-cement interlocking block compressive strength. Biotechnol. Agron. Soc. Environ.,2015, vol. 19 (3): 262-269.
Zander, R., et al., "Association Between Plasma Ionized Calcium and Lactate Concentration", Intensive Care Medicine, 1993, vol. 19, No. 6, pp. 362-363.
Zeolite as a Binding Agent for Ammonia Ions and as a Soil Additive. Part 1 Amonnia Adsorption by the Zeolite, Proceedings of the 5th Serbian-Croatian-Slovenian Symposium on Zeolites, J. Milovanovic et al., May 2013.
Zeynep Basaran Bundur et al., Biomineralized cement-based materials: Impact of inoculating vegetative bacterial cells on hydration and strength, Cement and Concrete Research 67:237-245 (2015). (Available online Oct. 27, 2014).
Zhao et al., Bioremediation of Cd by strain GZ-22 isolated from mine soil based on biosorption and microbially induced carbonate precipitation. Environ. Sci Pollut Res., 2017, Vo. 24: 372-380.
Co-pending U.S. Appl. No. 17/570,312, inventors Dosier; Ginger K. et al., filed Jan. 6, 2022.
Karthik et al. Properties of Bacterial-based Self-healing Concrete—A review. International Journal of ChemTech Research, vol. 9, No. 2, pp. 182-188 (2016).
Mendz et al. The urea cycle of Helicobacter pylori. Microbiology 142, 2959-2967 (1996).
PCT/US2011/033920 International Search Report and Written Opinion dated Aug. 2, 2011.
Pedersen et al. Evidence for bacterial urea production in marine sediments. FEMS Microbiology Ecology 12, 51-59 (1993).
U.S. Appl. No. 16/932,777 Office Action dated Mar. 24, 2022.
Van Paassen et al. Scale up of BioGrout: a biological ground reinforcement method. HAMZA et al., ed. Proceedings of the 17th International Conference on Soil Mechanics and Geotechnical Engineering, IOS Press, pp. 2328-2333 (2009).
Vijay et al. Bacteria based self healing concrete—A review. Construction and Building Materials 152:1008-1014 (2017). Available online Jul. 15, 2017.
Wei et al. Biomineralization processes of calcite induced by bacteria isolated from marine sediments. Brazilian Journal of Microbiology 46, 2, 455-464 (2015).
Ivanov et al. Sustainable and Safe Construction Biomaterials: Biocements and Biogrouts. Frontiers in Biomaterials, vol. 6, pp. 177-193 (2019).

\* cited by examiner

METHODS FOR THE MANUFACTURE OF COLORFAST MASONRY

REFERENCE TO RELATED APPLICATIONS

This application is a divisional of U.S. application Ser. No. 15/455,689, filed Mar. 10, 2017, now U.S. Pat. No. 10,717,674, which is a continuation-in-part of U.S. application Ser. No. 15/066,692 filed Mar. 10, 2016, which claims priority to U.S. Provisional Application No. 62/200,288 filed Aug. 3, 2015, U.S. Provisional Application No. 62/188,556 filed Jul. 3, 2015, and U.S. Provisional Application No. 62/130,854 filed Mar. 10, 2015, and claims priority to U.S. Provisional Application No. 62/358,937 filed Jul. 6, 2016, the entirety of each of which is hereby specifically incorporated by reference.

BACKGROUND

1. Field of the Invention

The invention is directed to kits, compositions, tools and methods for the manufacture of construction materials with artificial and/or added color. More particularly, the invention is directed to compositions, materials and methods for the manufacture of bricks and masonry blocks with a variety of colors, color patterns and colors that simulate natural materials such as bricks, cement and stone.

2. Description of the Background

Cement is manufactured from hydraulic calcium silicates containing calcium sulfate with other components. This composition is heated to high temperature and mixed with limestone, shale and other naturally occurring materials that are generally white or gray. These cements generally considered to be uncolored. The addition of pigments or dyes to uncolored cement creates a colored cement composition such as described in U.S. Pat. No. 4,204,876 which discloses a pigment containing thixotropic slurry that can be stored in drums for 6-12 months by a cement contractor and used in a batching system. Also, U.S. Pat. Nos. 5,558,708 and 5,846,315 disclose methods, composition and system for preparing pigmented cement compositions employing an aqueous component that contains a pigment and a dry powdered component. Other methods for preparing colored or pigmented cement compositions are described in U.S. Pat. Nos. 5,199,986, 3,667,976, and 4,946,505.

A product referred to as COLORQUARTZ is an aggregate that contains quartz particles ceramically coated by a process that permanently bonds inorganic pigments to the quartz particle. Particles are prepared by firing with intense heating at temperatures of 315° C. (600° F.) or higher. The particles are available in an S grade, which are spherical shaped particles and a T grade which are trowable particles, and are about 12-70 mesh or larger. The ceramically coated granules can be added to cement compositions such as plasters or flooring compositions to provide specks of color throughout the area or flooring, and do not provide a uniform color to the cement composition.

Gray cement can be prepared by employing a naturally occurring gray calcium carbonate product as an inert filler. The naturally occurring gray calcium carbonate exhibits a very high sulfur content that may adversely affects the final properties of the cured product, but the product is otherwise gray. Attempts at preparing colored cement compositions have included crushing naturally occurring colored marble, such as a green marble, and using the crushed colored marble as the inert filler in the cement composition. With this process, colors are limited and inhomogeneously dispersed and, accordingly, additional pigment is usually required with the problems and disadvantages associated therewith.

A disadvantage of preparing colored cement is that the pigment used to prepare the colored cement is typically dispersed throughout the fluid composition rather than being fixed to any of the solids in the composition and, thus, dispersion of the pigment leads to leaching while the cement is hydrating. In addition, the dispersion of pigments in cement compositions often results in color differences between batches due to variations in starting materials the fact that pigments tend to float to the surface.

SUMMARY OF THE INVENTION

The present invention overcomes problems and disadvantages associated with current strategies and designs and provides new tools, compositions and methods for the manufacture of colored solid structures such as bricks and masonry.

One embodiment of the invention is directed to methods for producing solid structures such as masonry containing any one or more of a variety of pigments and pigment combinations. Preferably, the method of the invention comprises combining a coloring agent (e.g., a pigment) with an aggregate material. Preferably the coloring agent is red, blue, green, yellow and/or combinations or varying hues and/or shades thereof. Compositions may also contain an identifying agent or a detectable marker such as a microscopic tag, a color, an enzyme or another substance. Coloring agents can be added to most any aggregate material. Preferably the aggregate comprises organic or inorganic material such as, for example, sand, rock, glass (e.g. Poraver), wood, paper, metal, plastic, polymers, minerals, recycled materials, or combinations thereof. Pigment may be added to aggregate as a liquid, gel, paste, or dry powder. Aggregate is preferably in the form of beads, grains, rods, strands, fibers, flakes, crystals, pulverized or crushed materials, or combinations thereof. Pigment is adhered to aggregate with a hydration of 5% or less, preferably 2% or less, and preferably 1% or less, and by agitation such as by mixing. Optionally, a small amount of liquid such may be added followed by another period of agitation, preferably to homogeneity. Once aggregate is colored, the colored aggregate is processed in accordance with procedures for the manufacture of calcite bonding between particles. The resulting solid structure contains the desired color or color combination, which may be uniform throughout the structure or of a design.

Another embodiment of the invention is directed to compositions comprising solid masonry containing any one or more of a variety of pigments and pigment combinations. Preferably the solid forms are blocks, boards, bricks, pavers, panels, tiles, or veneer, and the mixture further contains fibers or nanofibers that are, for example, fibers or nanofibers of wood, glass, plastic, metal or a polymer. Preferred fibers include, for example, polypropylene, HDPE, carbon fibers including high-strength carbon fibers, rayon, and biodegradable fibers such polymers of poly lactic acid, fibers of cellulose, minerals, chitin, and other plant materials. Solid structures may simulate natural materials such as, for example, slate, brick, marble, and other naturally occurring materials and especially construction materials. The pigmented solid structures made by the method of the invention do not leach pigment upon exposure to environmental conditions for a period of time preferably wherein the environmental conditions comprise one or more of rain, snow, visible light, rain, and temperature variations. Preferably the period of time is greater than ten years, and more preferably for the useful life of the masonry.

Another embodiment of the invention is directed to kits for manufacturing solid masonry forms with added color. Kits preferably comprise a composition comprising urease-producing spores or cells and a pigment, optionally an activating agent, and a nutrient media. Cells or cell spores may be encapsulated or coated with nutrient media such as, for example, proteins or polysaccharides, or polymers such as poly lactic acid which is water soluble. Preferably the nutrient media further contains additional urease producing cells, supporting cells, or spores.

Another embodiment of the invention is directed to methods for manufacture of solid forms comprising: mixing different sized or shaped aggregate material with pigment wherein, preferably, the pigmented aggregate material is largely composed of particulates of less than 5 mm in diameter. After mixing a small amount of a liquid, preferably water or another aqueous solution, is added and thoroughly mixed with the pigmented aggregate. The pigmented aggregate is processed in accordance with MICP to form calcite which, preferably, may be apportioned into multiple form works or extruded.

Other embodiments and advantages of the invention are set forth in part in the description, which follows, and in part, may be obvious from this description, or may be learned from the practice of the invention.

DESCRIPTION OF THE INVENTION

Traditional construction materials such as bricks and concrete require enormous amounts of energy during the manufacturing process. The colors of bricks and concrete most often reflect the color of the beginning aggregate which are often, for example, clay or a stone. Bricks and concrete can be artificially colored, but when colorants are added during manufacturing, the pigments remain in the liquid portion between particles of the aggregate. As the aggregate particles are compressed, such as with clay bricks, the spaces between particles diminish and the added color is virtually eliminated. With concrete, added color does not adhere to the particles and again, the natural color of the aggregate particles dominates forming a mosaic or colored cement and stone. Consequently, color changes of bricks and cement typically involve painting of the exposed surfaces. Painting requires repeated applications after periods of time with the periods determined by the quality of the paint and the conditions to which structures are exposed.

It is well established that an alternative to traditional brick making is available that consumes significant less energy and utilizes nearly any loose aggregate material as the base. This alternative employs natural microorganisms to manufacture bricks and/or masonry and can use most any base aggregate material. The process involves incubation of aggregate with enzymes that catalyze the precipitation of calcite. Traditionally, the solid forms created retain the color of the base aggregate or, like traditional bricks and cement, can be painted. It has surprisingly discovered that solid structures that are formed from microbial induced calcite precipitation (MICP) can be formed with most any color or color combination. In contrast to colored cement, according to the invention, pigment colors the aggregate surfaces and, thus, is visible throughout the finished solid and on all sides containing exposed aggregate. Solid structures thereby created can be uniform in color throughout, or colored in patterns or designs as desired.

An advantage of this process is that pigment is fixed to the surfaces of aggregate particles without the need for extreme heat or pressure and without the use of harsh chemicals. The process of the invention is preferably performed at ambient temperatures and pressures, and with no added chemicals as are typically used to create covalent bonds between pigment and aggregate surfaces. Heating of aggregate and pigment, if needed, is generally optional and typically utilized only with selected pigment chemical types. Another advantage of the invention is that the calcite, which forms between aggregate particles, is largely transparent and, as such, reflects the color of the pigmented aggregate particles thereby enhancing color intensity. Precipitated calcite further secures adherence of the pigment to the aggregate particles and also that the calcite crystals align the wavelength of reflected light.

Another advantage of the invention is that solid forms composed of the colored aggregate according to the invention retains a strong colorfastness. Colorfastness is at least as strong as painting and in most instances, the colorfastness of the solid is greater to and/or more resilient than as otherwise achieved from surface painting. Colorfastness was determined after exposure to simulated enhanced weathering conditions including exposure to sun, rain, heat, cold, salt, acid, base, and combinations thereof. As determined by visual analysis, there was no significant change or fading of color. Colorfastness was also determined by analyzing the pigment content of aqueous solutions after washing of the artificially colored solid structures including washing under pressure. Pigment was undetectable in effluent of the wash solutions. Colorfastness of solid forms manufactured according to the method of the invention is at least as colorfast as painted or stained bricks, cinder blocks or other construction materials. Preferably the colorfastness is retained for the useful life of the solid, which is preferably 10 years or more, 15 years of more, 20 years or more, 30 years or more, 50 years or more. As the pigment is a part of the masonry and believed to be affixed and effectively sealed with calcite bonds to aggregate surfaces, repeated painting is avoided and washing, if and when needed, does not alter colorfastness of the solid structure.

Another advantage of the invention is that solid structures can be manufactured with a desired hardness, load bearing capability and resistance to fracture. Load bearing was determined by standard procedures to measure the capability of the solid form to withstand weight and load without fracturing. By increasing the period of time for calcite formation and/or the number of cycles of calcite formation, hardness can be increased as desired. Hardness, load bearing capacity and resistance to fracture can be achieved that are equal to and greater than the same measure for comparable construction material such as bricks, pavers, cinder blocks and the like.

It has also been surprisingly discovered that solid structures that are formed from microbial induced calcite precipitation (MICP) according to the invention can be colored in a manner that simulates most any type of stone including, for example, bricks, slate, concrete, bluestone, granite, marble, and combinations thereof. As the solid structures of the invention can be manufactured with a variety of aggregate types and with various colors and color combination, those skilled in art can select aggregate type and colors or color combinations that simulate most any other material. In addition, this process allows for the creation of an unlimited number of designs and non-natural patterns as one may wish including, but not limited to combinations of different aggregate materials, combinations of different colors and combinations of designs and patterns of aggregates and/or colors.

One embodiment of the invention is directed to methods of producing artificially colored solid structures. In this method an aggregate material is selected and combined with a pigment. Preferably the aggregate material comprises most any type of natural rock or stone, glass, fiberglass, wood, biomass, paper, metal, plastic, polymers, rubber, imitation rubber, vinyl, minerals, imitations of rock or stone, recycled materials such as, for example, recycled brick, concrete, stone, mine tailings and mining residues, scrubber wastes, and/or combinations thereof. Aggregate can be of any size including mixtures of sizes provided such aggregate is smaller in size than the resulting structure. Preferably aggregate materials are particles of aggregate of 10 mm or less, 5 mm or less, 1 mm or less, 0.5 mm or less, or combinations thereof. Mesh sizes can be as desired including but not limited to very fine particles (any number between and including 32-300 standard mesh), fine particles (any number between and including 10-32 standard mesh), medium particles (less than 10 standard mesh including all mesh numbers therein), and coarse particles (particles greater than or equal to 2 mm), and combinations thereof. Particle can be most any shape including, for example, round or rounded, oval, spherical (S grade), square, rectangular, hedral, fiber, lath, angular, elongated, needle-like, acicular, flat, flaky, cylindrical, spongy, cubic, cubical and combinations and variations thereof. If desired or necessary, aggregate particles can be roughened to create cracks in and crevices on particle surfaces. Roughening can be performed by mixing particles together in a mixer or blender with sufficient force to create cracks in and crevices on particle surfaces, by adding ball bearings or another substance to the aggregate particles with a hardness equal to or greater than the particles themselves, by passing particles over a roughening agent such as, for example, sand, steel, or industrial diamonds, or another roughening agent known to those skilled in the art or combinations thereof.

A pigment is any material that changes the color of reflected or transmitted light as the result of wavelength-selective absorption. According to the invention, the term pigment also includes materials that create fluorescence, phosphorescence, luminescence or another form or artificial color in which the resulting solid structure emits selected light waves. Pigments that can be utilized include organic pigments, inorganic pigments, synthetic pigments, metallic pigments, lake pigments, biological pigments, pigments obtained or derived from plants, animals and/or bacteria, natural pigments, mineral pigments, and combinations thereof. A listing of selected pigments (all commercially available) useful for the invention is provided in Table 1.

TABLE 1

Purple pigments

Aluminum pigments
Ultramarine violet: (PV15) Silicate of sodium and aluminum containing sulfur.
Copper pigments:
Han Purple: $BaCuSi_2O_6$.
Cobalt pigments:
Cobalt Violet: (PV14) cobaltous orthophosphate.
Manganese pigments:
Manganese violet: $NH_4MnP_2O_7$ (PV16) Manganic ammonium pyrophosphate TABLE 1-continued Phthalo pigments:
Phthalocyanine
Blue pigments Aluminum pigments:
Ultramarine (PB29): a complex naturally occurring pigment of sulfur-containing sodio-silicate ($Na_{8-10}Al_6Si_6O_{24}S_{2-4}$); lapis; lazule
Cobalt pigments:
Cobalt Blue (PB28) and Cerulean Blue (PB35): cobalt(II) stannate
Copper pigments:
Egyptian Blue: a synthetic pigment of calcium copper silicate ($CaCuSi_4O_{10}$).
Han Blue: $BaCuSi_4O_{10}$
Iron pigments:
Prussian Blue (PB27): a synthetic pigment of ferric hexacyanoferrate ($Fe_7(CN)_{18}$). The dye Marking blue is made by mixing Prussian Blue and alcohol.
Manganese pigments:
YInMn Blue: a synthetic pigment ($YIn_{1-x}Mn_xO_3$)
Green pigments Cadmium pigments:
Cadmium Green: a light green pigment consisting of a mixture of Cadmium Yellow (CdS) and Viridian ($Cr_2O_3$)
Chromium pigments:
Chrome green (PG17): chromic oxide ($Cr_2O_3$)
Viridian (PG18): a dark green pigment of hydrated chromic oxide ($Cr_2O_3 \cdot H_2O$)
Copper pigments:
Azurite: cupric carbonate hydroxide ($Cu_3(CO_3)_2(OH)_2$)
Malachite: cupric carbonate hydroxide ($Cu_2CO_3(OH)_2$)
Paris Green: cupric acetoarsenite ($Cu(C_2H_3O_2)_2 \cdot 3Cu(AsO_2)_2$)
Scheele's Green (also called Schloss Green): cupric arsenite ($CuHAsO_3$)
Verdigris: various poorly soluble copper salts, notably cupric acetate ($Cu(CH_3CO_2)_2$) and malachite ($Cu_2CO_3(OH)_2$)
Yellow pigments Arsenic pigments:
Orpiment natural monoclinic arsenic sulfide ($As_2S_3$),
Cadmium pigments:
Cadmium Yellow (PY37): cadmium sulfide (CdS)
Chromium pigments:
Chrome Yellow (PY34): natural pigment of plumbous chromate ($PbCrO_4$).
Cobalt pigments:
Aureolin(also called Cobalt Yellow) (PY40): Potassium cobaltinitrite ($Na_3Co(NO_2)_6$).
Iron Pigments:
Yellow Ochre (PY43): a naturally occurring clay of monohydrated ferric oxide ($Fe_2O_3 \cdot H_2O$)
Lead pigments:
Naples Yellow (PY41); lead-tin-yellow
Titanium pigments:
Titanium Yellow (PY53)
Tin Pigments:
Mosaic gold: stannic sulfide ($SnS_2$)
Orange pigments Cadmium pigments:
Cadmium Orange (PO20): an intermediate between cadmium red and cadmium yellow: cadmium sulfoselenide.
Chromium pigments:
Chrome Orange: a naturally occurring pigment mixture composed of lead (II) chromate and lead (II) oxide. ($PbCrO_4$ + PbO)
Red pigments Cadmium pigments:
Cadmium Red (PR108): cadmium selenide (CdSe)
Iron oxide pigments:
Sanguine, Caput Mortuum, Venetian Red, Oxide Red (PR102)
Red Ochre (PR102): anhydrous $Fe_2O_3$
Burnt Sienna (PBr7): a pigment produced by heating Raw Sienna.
Lead pigments:
Red Lead: lead tetroxide, $Pb_3O_4$
Mercury pigments:
Vermilion (PR106): Synthetic and natural pigment: Occurs naturally in mineral cinnabar. Mercuric sulfide (HgS)

TABLE 1-continued

Brown pigments

Clay earth pigments (naturally formed iron oxides)
Raw Umber (PBr7): a natural clay pigment consisting of iron oxide, manganese oxide and aluminum oxide: $Fe_2O_3$ + $MnO_2$ + $nH_2O$ + Si + $AlO_3$. When calcined (heated) it is referred to as Burnt Umber and has more intense colors.
Raw Sienna (PBr7): a naturally occurring yellow-brown pigment from limonite clay.

Black pigments

Carbon pigments:
Carbon Black (PBk7)
Ivory Black (PBk9)
Vine Black (PBk8)
Lamp Black (PBk6)
Iron Pigments:
Iron black (PBk11) (C.I. No.77499): $Fe_3O_4$
Titanium pigments:
Titanium Black ( ): Titanium(III) oxide ($Ti_2O_3$)

White pigments

Antimony pigments:
Antimony White: Stibous Oxide ($Sb_2O_3$)
Barium pigments:
Barium sulfate (PW5): ($BaSO_2$)
Lead pigments:
Cremnitz White (PW1): basic Plumbous Carbonate (($PbCO_3)_2 \cdot Pb(OH)_2$)
Titanium pigments:
Titanium White (PW6): Titanic Oxide ($TiO_2$)
Zinc pigments:
Zinc White (PW4): Zinc Oxide (ZnO)

Other pigments

Fluorescent pigments
Luminescent pigments
Phosphorescent pigments
Organic pigments
Biologically-Derived pigments Pigments may be provided dry, such as in powder form, in a gel, as a paste, or suspended in solution (e.g., polar or non-polar, aqueous or non-aqueous). The amount of pigment added to the aggregate is from 1 mg to 10 g (dry weight) per kg of aggregate (dry weight), preferably from 10 mg to 1 g (dry weight) per kg of aggregate (dry weight), and also preferably from 10 mg to 100 mg (dry weight) per kg of aggregate (dry weight). The amount of pigment added is dependent on the type of aggregate, the form of aggregate (e.g., particle shape and size), the pigment selected, and also the desired color intensity of the final product. Preferably, pigment is thoroughly mixed to homogeneity with the aggregate materials selected prior to the formation of calcite. Also preferably the pigment plus aggregate mixture has a fluid content of 5% by weight or less, more preferably 4% by weight or less, more preferably 3% by weight or less, more preferably 2% by weight or less, more preferably 1% by weight or less, and more preferably 0.5% by weight or less. Fluid is preferably water, steam or an aqueous liquid, but, depending on the pigment selected, may be a polar or non-polar solvent such as benzene, dimethylsulfoxide (DMSO), an alcohol (e.g., methanol, ethanol, butanol, isopropyl) or combination thereof. Mixing is preferably non-violent so as to minimize collisions between particles of a force that would prevent adherence of pigment, but sufficiently thorough so that pigment is able to adhere to particle crevices and surfaces as desired. Typical mixers include static mixers, rotating drums, tumblers, blenders, vessels containing rotating paddles or sticks, professional mixers, hand mixers, stirring apparatuses, electric mixers and the like. Mixing is preferably performed to achieve homogeneity so that an even layer of pigment exists over all or most particles.

Once pigment has been adhered to aggregate particles, optionally a small amount of fluid, preferably water, is added to the mixture and the mixture is once again thoroughly mixed preferably to homogeneity. The amount of fluid added is preferably 5% by weight or less, more preferably 3% by weight or less, more preferably 2% by weight or less, more preferably 1% by weight or less, and more preferably 0.5% by weight or less. The fluid plus pigmented aggregate mixture is preferably mixed using the same apparatus as was used to mix pigment and aggregate. Once the fluid, and pigmented aggregate is thoroughly mixed, the aggregate is processed to a solid structure using enzymes as disclosed and described in U.S. Pat. Nos. 8,728,365; 8,951,786 and 9,199,880 (all of which are specifically and entirely incorporated by reference).

Briefly, a urea source, a calcium source and an enzyme source and/or optionally the nutrient content when using urease-producing cells (e.g., spores, bacterial cells, etc.) are added to the aggregate and incubated for a period of time to allow for the formation of calcite bonds between particles. The amount of calcite formed between particles of aggregate can be increased or decreased to create a desired level of hardness to the structure. Variations can be achieved by varying the amounts of calcium, urea, enzyme and/or nutrients, and/or varying the time of incubation or numbers of incubation cycles. Typically, urease-producing cells are aerobic and include, for example, *Sporosarcina pasteurii, Sporosarcina ureae, Proteus vulgaris, Bacillus sphaericus, Myxococcus xanthus, Proteus mirabilis, Helicobacter pylori* and other strains, serotypes, variations, mutations and CRISPR modifications (clustered regularly interspaced short palindromic repeats). Cells produce the enzyme urease which, in the presence of calcium and nitrogen sources, forms calcite crystals under a process generally referred to as microbial induced calcite precipitation (MICP), which can be performed with the activated cells or purified enzyme. When using spores, an activating agent can be added to stimulate conversion of spores to active cells. Typical activating agents include, for example, cellular nutrients such as amino acids, saccharides and polysaccharides.

The enzymes and/or the enzyme-producing cells or spores are dispersed in a composition containing the pigmented aggregate, urea, and calcium chloride. The composition may include or be combined with a support material which may be organic or inorganic and is preferably a solid or semi-solid and preferably contains holes or perforations and/or is otherwise porous. Organic support material includes, for example, biomass such as, preferably, moss, hay, straw, grass, sticks, leaves, algae, dirt, dust, particulate material, refuse and combinations thereof. Fibrous materials include sheets or tarps of burlap, paper, wood, cotton, or another natural fiber. Non-natural and manufactured materials may also be used such as, for example, sheets of plastic, glass, fiberglass, vinyl, rubber, steel, iron or combinations thereof. To the solid support optionally may be applied otherwise may be introduced other cells would be useful to support the grown of the urease-producing cells or enhance the chemical processes involved and not otherwise interfere with the MICP process. Cells can be proliferated directly on the support material and, at a desired density or growth stage, the organic material evenly dispersed and/or thoroughly mixed into an aggregate material for manufacture of construction tools and products. Inorganic materials that can be used include, for example, rock, sand, glass, wood, paper, metal, plastic, polymers, and minerals, any of which can be crushed or used whole or combinations thereof with an aggregate material catalyzing the production of ammonia and carbon dioxide, increasing the pH level of the composition. The rise in pH forms a mineral precipitate combining calcium with carbon dioxide. The cells or other particles act as nucleation sites, attracting mineral ions from the calcium to the particle surfaces forming calcium carbonate crystals such as calcite crystals or other calcium carbonate polymorphs. The mineral growth fills gaps between the particles of aggregate, bio-cementing or bonding aggregate particles forming a solid. This manufacturing method through induced cementation exhibits low embodied energy, and can occur at ambient pressure, and in a range of temperatures from at least minus 20° C. to above 80° C. Preferably, the temperature range is below 30° C., below 40° C., below 50° C., below 60° C., or below 70° C. The ambient temperatures and conditions as well as the content of available aggregates can determine whether pure enzyme, lyophilized enzyme, spores, or live cells are utilized as the starting components. Living cells can be used in temperatures where mild weather conditions exist, whereas pure enzymes can be advantageous at more extreme conditions of cold or heat. Spores are used when immediate calcification is not required and the spores are provided sufficient time to germinate and express enzyme.

Mixtures of colored aggregate, microbes and/or enzymes, urea, calcium and nutrients are incubated for one or more periods of time. Preferably an incubation is for one or more hours, two or more hours, three or more hours, four or more hours, five or more hours, six or more hours, seven or more hours, eight or more hours, nine of more hours, ten or more hours, eleven of more hours, twelve or more hours, or longer. The length of time of an incubation is largely determined by the size of the solid structure being formed, temperature, the amount of nutrients provided and also the amount of substrate provided. Accordingly, incubation times can be increased or decreased as desired by varying one or more of these parameters.

The resulting solid structures exhibit a hardness and physical properties suitable for use in the construction of structures and whose hardness can be predetermined or preselected as desired. Hardness of the solids formed according to the invention can be at least as hard as or greater than natural brick, natural cement and any variations thereof. Solids manufactured according to the invention can be structural with supporting necessary hardness requirements and/or be decorative.

Another embodiment of the invention is directed to the artificially colored solid structures manufactured according to the methods of the invention. Solid structures can be nearly any color or color combination as desired. As such, another embodiment of such structures and solids that simulate the appearance of other solids such as, for example, stone, slate, marble, brick, granite, solid construction materials, solid decorative materials, and combinations thereof. Solid structures are formed by the MICP process according to the invention, but using selected aggregate, aggregate particles sizes, and one or more pigments. The aggregate and pigments are selected and combined as described herein prior to the MICP process. By selecting aggregate with a fine particle size and gray, blue and black pigments, a simulated slate product can be formed. Fine particles and a variety of different colors and colored combinations of aggregate can be used to create simulated slate. Simulated bricks are manufactured using coarse aggregate which has been pigmented with iron oxide. Pigment variations as found in natural brick can be created by sprinkling a variety of black aggregate into the iron oxide-dyed aggregate prior to the MICP process. Surface texturing can gave the appearance of a different substance such as, for example, grinding a surface smooth and with pigment variations such as veining can provide the appearance of marble. Etching surfaces can provide an appearance of shale. Variations of aggregate type coupled with dots or sparkles of color can provide the appearance of granite. Any number of shapes and textures can be created for decorative purposes as well.

Support materials and/or aggregate material may contain additional components that provide an advantage to the construction materials. For example, chemicals and/or additional cell (e.g., bacteria, yeast, eukaryotic cell, algae, and recombinant variations thereof), can be included that produce enzymes and/or other chemicals useful in breaking down stains in and/or acquired by the final product. Stains include stains from air pollution, soot, mold or animal waste products. Alternatively, the chemical or enzymes may impart color, texture or a desired function or appearance to the final product.

Another embodiment of the invention is directed to kits for manufacturing artificially colored solid forms comprising one or more of: colored aggregate materials of the invention or a composition for coloring aggregate containing one or more pigments, a composition containing nutrients for proliferation of the ureases-producing cells and/or germination of the cell spores; a composition containing agents for stimulation of spores to a vegetative state and/or urease production; a plurality of sets of formworks wherein each set encloses the shape of at least one solid form and contains one or more porous panels; and a third composition comprising a calcium source (e.g., $CaCl_2$), a nitrogen source (e.g., urea) or both a calcium source and a nitrogen source. Preferably the kit is for the creation of solid forms such as, for example, rectangular, square, rounded, oval or an irregular shape. Preferred solid forms include but are not limited to blocks, boards, bricks, pavers, panels, tiles, counter tops, or veneer. Preferably kits of the invention are for the manufacture of blocks such as, for example, concrete masonry, cinder blocks, foundation blocks, breeze blocks, hollow blocks, solid blocks, besser blocks, clinker blocks, high or low density blocks, or aerated blocks. Nutrient compositions of the invention may contain nutrient media to maintain and/or allow the cells to flourish and proliferate. The various types of nutrient media for cells, and in particular, bacterial cells of the invention are known and commercially available and include at least minimal media (or transport media) typically used for transport to maintain viability without propagation, and yeast extract, molasses, and corn steep liquor, typically used for growth and propagation. Preferably the nutrients and/or the agents to stimulate vegetative propagation include one or more of amino acids, proteins, polysaccharides, fatty acids, vitamins and minerals. Preferably form works comprise wood, plastic, composite materials, gel, foam, powder, or another material that maintains separation of aggregate material into forms, wherein nutrients can be provided and metabolic waste materials drained away.

Another embodiment of the invention is directed to methods for manufacture of solid forms comprising: mixing the composition of the invention with an artificially colored aggregate material and water to form a mixture, wherein the aggregate material is largely composed of particulates of less than 5 mm in diameter (e.g. less than or about 4 mm, less than or about 3 mm, less than or about 2 mm, or less than or about 1 mm); apportioning the mixture into multiple form works wherein each form work contains at least one porous panel; adding a second composition to the mixture, wherein the second composition contains nutrients that promote proliferation of the urease-producing cells; adding a third composition to the mixture, wherein the third composition is a liquid, powder or paste that contains calcium; incubating the mixture for a period of time to form covalent bonds between the particulates; and removing the solid forms from the form works. Alternatively, the compositions may be combined and added together to the material within the form works or combined with the material prior to addition to the form works.

Another embodiment of the invention is directed to the structure and composition of form works. Preferred form works comprises a thermoplastic material that can be molded or extruded into a desired shape. Preferred thermoplastics include, but are not limited to plastics such as polypropylene, polystyrene, polyethylene including HDPE (high density polyethylene), LPDE and reclaimed LDPE (low density polyethylene), and cross-linked polyethylene, glass and most any formable polymer. Preferably, the polymer material is provided as pellets or lens shapes that range in thickness and uniformity. The pellets are filled in a porous mold and steamed under pressure (the mold is not under pressure, pressure just from the steam). The resulting product provides a designed flow directional material, and changes to the gradation impact the flow direction, speed and retained saturation. Shapes may be pressed with temporary binder and tops shaded without the need of formworks.

Preferably the multiple form works comprises 5, 10, 50, 100, 500, 1,000, 10,000, 100,000, 1,000,000 or more forms at a time. The number of form works that can be simultaneously treated is limited only by the complexity of the mechanics and space available. These form works may be stacked or provided in a single layer or pallet. Formwork may have vertical walls which are connected together forming cavity there between to receive the aggregate material. Formworks may also have a floor and, alternatively, the bottom of the formwork may be left open if supported by a porous surface such as soil, or aggregate and composition may be mixed and pressed into molds or extruded. Preferably, vertical walls are at least the inside surfaces thereof, are made of a non-reactive, non-porous material or coating such as cast or extruded acrylic resin. This enables one to easily remove the construction material or the brick from the formwork after it has solidified. In addition, the vertical walls and floor of formwork may have textures to form textures in the resulting brick.

Preferably the colored aggregate material comprises rock, stone, glass, fiberglass, wood, biomass, paper, metal, plastic, polymers, rubber, imitation rubber, vinyl, minerals, recycled material including any of the aforementioned materials or combinations thereof, and/or mixing comprising spraying the composition as a liquid onto the aggregate material. Preferably the form works are substantially submerged during the incubating and air is bubbled to the submerged form works. Preferably a third composition is added to the mixture repeatedly during incubating which drains through the bottom panel and, optionally, is recycled. Preferably, incubating is performed under ambient conditions and the third composition contains calcium chloride, calcium acetate, calcium phosphate, calcium carbonate, calcium lactate, calcium nitrate, or a calcium salt. Preferably the pH of the mixture is monitored during the incubating. Preferably the solid forms are blocks, boards, bricks, pavers, panels, tiles, or veneer, and the mixture further contains fibers or nanofibers that are, for example, fibers or nanofibers of wood, glass, plastic, metal or a polymer. The solid forms can be partially or uniformly porous containing a network of holes or gaps. Holes can be of a predetermined size and/or structure such as, for example, at least 5 microns, at least 10 microns, at least 20 microns, or at least 50 microns in diameter. Alternatively, solid forms can be manufactured with materials that provide virtually no or few holes. For example, adding a non-porous material to the aggregate mixture can create complex and extended pathways that render the form impermeable to fluids.

Another embodiment of the invention comprises compositions containing urease producing cells or cell spores that are coated with nutrient media and contain a coloring agent or pigment. Preferably the nutrient media further contains additional urease producing cells or cell spores, and/or nutrients to promote the proliferation of additional cells that have been added to the aggregate that are beneficial to the final product. Also preferably the coloring agent or pigment maintain the cells and/or spores in an inactive and/or dormant state for transportation and/or storage.

Another embodiment of the invention is directed to compositions, methods and systems for the treatment of artificially colored aggregate materials comprised of particles with a composition comprising one or more of a nitrogen source such as for example urea, a calcium source (e.g., calcium ions) and urease or urease producing cells. Preferably particles have a diameter (e.g., actual, average or effective diameter) of less than 1 mm and preferably less than 0.5 mm, more preferably less than 0.1 mm and more preferably less than 50 μm. Especially preferred particles sizes include from 10 μm to 1 mm, from 100 μm to 0.5 mm, from 200 μm to 1 mm and various combinations thereof. Particles include, for example, spores, carbon dust, dust or soot from cement or brick manufacture, cement block manufacture, foundry operations, grinding limestone, sand tailings, mining, smelters, paint manufacturing and byproducts of other manufacturing processes such as slag. Particles may be obtained and collected from available or implemented dust control procedures. Particles may be of mixed sizes including but not limited to sizes equal to and greater than preferred sizes, particles equal to and less that preferred sizes, and combinations of preferred sizes and mixtures thereof. Particles that are aggregates and more sizable particles may include recycled and/or recyclable materials. The nitrogen source of the composition may be a single chemical, such as urea of any grade and purity and is preferably commercially obtained. Calcium ions are preferably obtained from commercially available sources such as, for example, calcium chloride. Urease enzyme or urease-producing bacteria may be included in the composition. Urease-producing bacteria include, but are not limited to the bacteria *Sporosarcina Pasteurii, Sporosarcina Ureae, Proteus Vulgaris, Bacillus Sphaericus, Myxococcus Xanthus, Proteus Mirabilis, Helicobacter Pylori* and combinations thereof. Urease producing cells includes non-viable cells that contain enzyme such as, for example, mycells, cells composed of lipids or fatty acids, and cells containing urease. Urease and/or urease-producing cells may produce or release a predetermined amount of enzyme over a defined period of time. Preferably, the amount of urease released per cell is sufficiently rapid to allow for the rapid creation of calcium carbonate in the presence of nitrogen and calcium ions.

Preferably, the colored particles are combined with a nitrogen source (e.g., urea), urease and/or urease producing cells, calcium ions and preferably water to create a homogenous slurry. The slurry can be painted or sprayed onto objects and/or surfaces creating a layer or crust, molded into forms that solidify into objects which may be complete or partially solid, or otherwise pooled for immersion or dipping of objects to be coated with the slurry material again creating layers or a crust over the object surfaces. Objects may contain one or more layers as desired, and layers may be permeable or impermeable to water or improve resistant to wear from weather conditions such as sun damage, snow, ice and rain. Slurries that provide increased resistance are preferably composed with aggregate materials that are particles of less than 0.1 mm diameter. As the liquid dries, calcium carbonate bonds form between the particles and/or the particles and the object. The result can be an object containing an outer shell of hardened calcium carbonate or a formed structure. Objects that can be manufactured according to the invention and/or layered with a crust or coating of the invention include, but are not limited to bricks, cement blocks, pavers, counter tops, glass, fiberglass, polymer and acrylic structures, siding, walls, yard art, slate and rock structures, tiles, paving stones, steps, roofing material, gutters, cement walls and planks, patios, balconies, fencing and combinations thereof.

The following examples illustrate embodiments of the invention, but should not be viewed as limiting the scope of the invention.

EXAMPLES

Example 1 Loose Aggregate Study

A loose aggregate sample was collected and was tested for color fastness with tap water, dish soap, and 10% sodium hypochlorite (concentrated bleach). Four small samples of the aggregate were placed into a 100 mL sample collection cups and each rinsed with a different type of solution until the liquid ran clear.

Some pigment was removed from the aggregate with all solutions, however for the tap water and dish soap it seemed that only any loose pigment was removed, the overall color of the dyed aggregate remained the same. The bleach solution removed more color from the aggregate, which remained a dark red albeit slightly lighter than the tap water and dish soap samples. Although bleach would remove some color from the aggregate, tap water and normal dish soap had little effect on color fastness of loose pigmented aggregate.

Example 2 Biologically Cemented Aggregate and Portland Cement Concrete Comparative Study Two pigmented biologically cemented units and two pigmented concrete thin facing bricks were selected to test color fastness. One of each of the units were partially submerged (about 50%) in 10% sodium hypochlorite and the other units were placed in ALCONOX (all-purpose industrial detergent) at a concentration of 1 g ALCONOX to 700 mL of tap water. All of the units were removed from their respective solutions after a few hours and scrubbed with a hard bristled brush to attempt to remove as much color as possible. Fresh solutions were made and the units were placed back into their respective solutions. The units sat in the solutions for a total of 46 hours for the biologically cemented test units and 42.5 hours for the concrete units. The biologically cemented test unit in bleach exhibited very little color change as compared to the unsubmerged portion of the unit. The concrete units exhibited removal of surface coloring by scrubbing with either bleach or ALCONOX to the point where some of the aggregate was visible behind the color.

Overall color fastness of biologically cemented test units was superior to that of uncemented pigmented aggregate. As compared to the concrete units, the biologically cemented test units show greater abrasive colorfastness.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A biocement composition comprising urease producing microorganisms, a pigment, an aggregate material, and calcium carbonate, wherein individual particles of the aggregate material are bound to each other by the calcium carbonate and wherein the pigment is affixed to the surface of particles of the aggregate by the calcium carbonate.

2. The composition of claim 1, wherein the microorganisms comprise one or more of parasites, eukaryotic cells, bacterial cells, algae and spores.

3. The composition of claim 2, wherein the microorganisms are encapsulated, microencapsulated or coated with nutrients, proteins, polysaccharides, or polymers.

4. The composition of claim 1, wherein the pigment is a powder, a paste, a gel or an aqueous solution.

5. The composition of claim 1, wherein the pigment comprises purple, blue, orange, green, yellow, red, brown, black and/or white pigments.

6. The composition of claim 1, wherein the aggregate material comprises rock, stone, glass, fiberglass, wood, biomass, paper, metal, plastic, polymers, rubber, imitation rubber, vinyl, minerals, imitations of rock or stone, recycled materials such as, for example, recycled brick, concrete, stone, mine tailings, mining residues, scrubber wastes, or combinations thereof.

7. The composition of claim 1, wherein the aggregate material comprises particles having a particle shape selected from the group: round, rounded, oval, spherical (S grade), square, rectangular, hedral, fiber, lath, angular, elongated, needle-like, acicular, flat, flaky, cylindrical, spongy, cubic, cubical and combinations and variations thereof.

8. The composition of claim 7, wherein the particles comprise very fine particles, fine particles, medium particles and coarse particles, wherein very fine particles have a standard mesh size from 32-300; fine particles have a standard mesh size from 10-32; medium particles have a standard mesh size from 1-10; and coarse particles have a size greater than or equal to 2 mm.

9. The composition of claim 1, where in the pigment comprises a pigment selected from the group of chrome orange, cadmium red, sanguine, caput mortuum, venetian red, oxide red, red ochre, burnt sienna, red lead, vermillion, clay earth pigments, raw umber, burnt umber, raw sienna, carbon black, ivory black, vine black, lamp black, iron black, titanium black, antimony white, barium sulfate, cremnitz white, titanium white, zinc white, fluorescent pigments, luminescent pigments, and phosphorescent pigments.

10. The composition of claim 2, wherein the urease producing organisms comprise *Sporosarcina pasteurii, Sporosarcina ureae, Proteus vulgaris, Bacillus sphaericus, Myxococcus xanthus, Proteus mirabilis, Helicobacter pylori* and other strains, serotypes, variations, mutations, CRISPR modifications and combinations thereof.

11. The composition of claim 1, further comprising fibers or nano-fibers.

12. The composition of claim 11, wherein the fibers or nano-fibers comprise polypropylene fibers, HDPE fibers, carbon fibers, high-strength carbon fibers, rayon fibers, biodegradable polymer fibers, poly lactic acid fibers, fibers of cellulose, mineral fibers, chitin, plant fibers, or combinations of one or more thereof.

13. The composition of claim 1, wherein the composition resists leaching of pigment for a period of time when exposed to environmental conditions.

14. The composition of claim 13, wherein the environmental conditions comprise one or more of rain, snow, visible light, rain, and temperature variations.

15. The composition of claim 14, wherein the period of time is the useful life of masonry made from the composition.

16. The composition of claim 13, wherein the period of time comprises ten years or more.

17. The composition of claim 1, wherein the urease producing organisms comprise *Sporosarcina pasteurii* and the pigment is a powder.

18. The composition of claim 17, wherein the aggregate material comprises rock, stone minerals, imitations of rock or stone, recycled materials such as, for example, recycled brick, concrete, stone, mine tailings, mining residues, scrubber wastes, or combinations thereof.

* * * * *